United States Patent [19]

Kuhn

[11] 3,935,355
[45] Jan. 27, 1976

[54] WRAPPING MATERIAL
[76] Inventor: Hans Georg Kuhn, Heerstrasse 131/135, D-1000 Berlin 19, Germany
[22] Filed: Dec. 20, 1972
[21] Appl. No.: 317,056

[30] Foreign Application Priority Data
Dec. 28, 1971 Austria.............................. 11166/71

[52] U.S. Cl................ 24/150 R; 128/90; 128/156; 128/290 W; 174/122 G; 174/124 G; 174/110 SR; 174/120 SR; 174/121 SR; 428/138; 428/152; 428/223; 428/236; 428/246; 428/251; 428/252; 428/253; 428/285; 428/913
[51] Int. Cl.² ....................................... B32B 3/10
[58] Field of Search .......... 161/410, DIG. 1, 92, 93, 161/DIG. 4, 127, 77; 128/290 W, 290 R, 290 P, 155, 156, 90, 89, 87; 206/219; 428/138, 139, 140, 152, 230, 236, 246, 251, 252, 253, 273, 284, 285, 287, 431, 913, 223; 174/110 SR, 120 R, 120 C, 120 SR, 121 R, 121 SR, 121 G, 124 G, 124 GC

[56] References Cited
UNITED STATES PATENTS

| 3,072,512 | 1/1963 | Dalle..................................... 161/92 |
| 3,332,416 | 7/1967 | Brickman et al. .................. 128/156 |
| 3,373,741 | 3/1968 | Hill et al............................. 128/156 |
| 3,415,243 | 12/1968 | Sheldon................................. 128/90 |
| 3,468,311 | 9/1969 | Gallagher............................. 128/296 |
| 3,481,821 | 12/1969 | Brunner et al....................... 161/53 |
| 3,523,056 | 8/1970 | Horning............................... 428/230 |
| 3,597,300 | 8/1971 | Miller ................................... 161/92 |
| 3,607,530 | 9/1971 | Carpenter............................. 156/64 |
| 3,666,615 | 5/1972 | Iwai et al. ....................... 161/DIG. 1 |
| 3,674,021 | 12/1970 | Snyder et al........................... 128/90 |
| 3,756,389 | 9/1973 | Firth ................................... 206/47 A |

FOREIGN PATENTS OR APPLICATIONS
870,150    5/1971   Canada................................ 128/90

Primary Examiner—George F. Lesmes
Assistant Examiner—S. Silverman
Attorney, Agent, or Firm—Steinberg & Blake

[57] ABSTRACT

An elongated wrapper which is initially flexible and which, when wrapped around one or more bodies, is adapted to be stretched and assume a substantially rigid condition. The wrapper has an outer, elongated, tubular, elastic envelope assembly which is of a generally flat cross section and which is adapted to surround one or more bodies while being longitudinally stretched and wrapped around the bodies. This envelope assembly has an inner surface carrying one of a pair of materials which, when they combine, react to assume a hardened condition. The other of these materials is situated in the interior of the envelope assembly and is separated from the one of the pair of materials by a separating layer structure which is located in the envelope assembly between the pair of materials separating them from each other to prevent them from combining. This separating layer assembly has the property of responding to the longitudinal stretching of the envelope assembly when the latter is wrapped around one or more bodies to assume a non-separating condition placing the materials in contact with each other so that they will then combine to assume the hardened condition.

32 Claims, 6 Drawing Figures

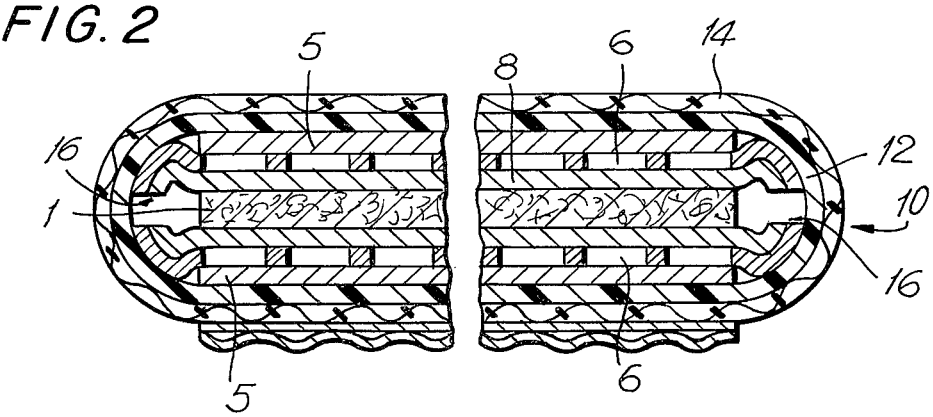
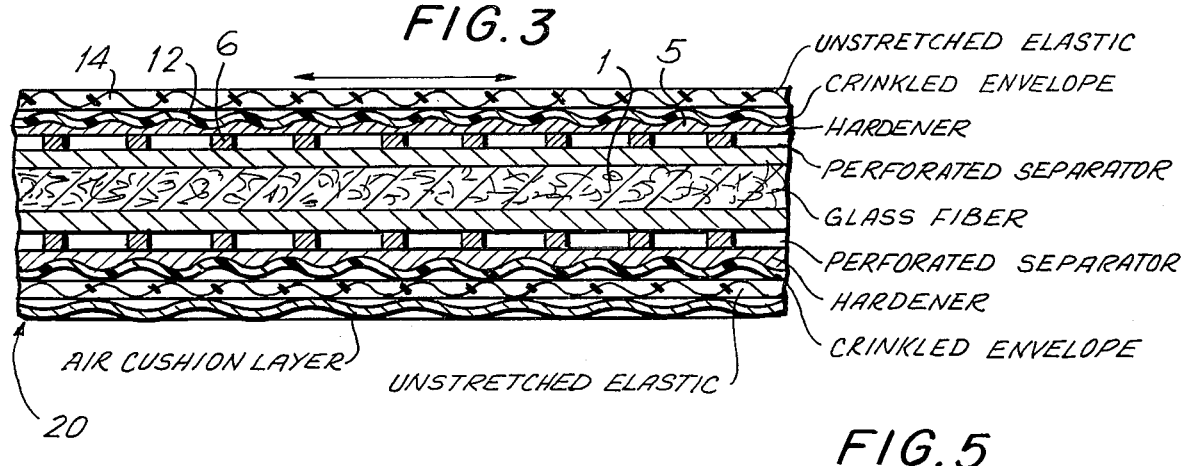
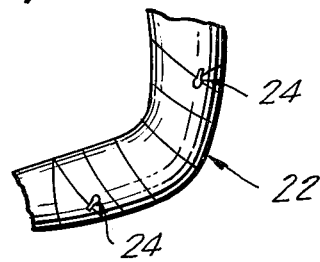
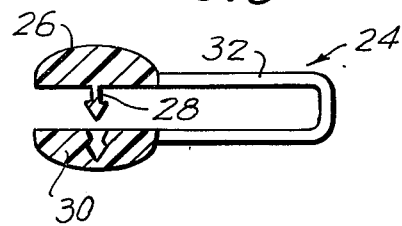
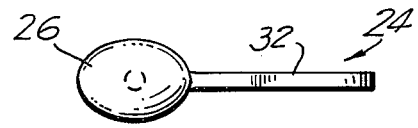

WRAPPING MATERIAL

BACKGROUND OF THE INVENTION

The present invention relates to wrappers.

Thus, the present invention relates to wrappers in the form of ribbons, tapes, bandages, or the like, which are adapted to be wrapped around one or more bodies for a number of different purposes.

For many different purposes it is desirable to have a wrapper of the above general type which is capable of being wrapped around one or more bodies and which then is capable of assuming a hardened condition. For this purpose it is known, for example, to provide a fleece layer of glass fibers impregnated with polyester and situated in a plastic envelope which also contains a hardener for the polyester, the hardener being separated from the polyester and being situated in its own envelope which is ruptured when the wrapper is used so that the hardener is released to combine with the polyester.

Known structures of this latter type have the disadvantage of a non-uniform mixing of the hardener and polyester with development of temperatures which are too high so that the desirable mechanical properties are not achieved with the hardened polymer because of brittleness on the one hand and flexibility on the other hand. A further disadvantage of the known structures of the above type is that the envelope has no elasticity or deformability so that it cannot conform to the configuration of the body on which the wrapper is wound.

SUMMARY OF THE INVENTION

It is accordingly a primary object of the present invention to provide a wrapper which will avoid the above drawbacks. Thus, it is an object of the present invention to provide a wrapper which is in its entirety elastically deformable so that it will conform to any configuration of a body on which the wrapper is wound.

Furthermore, it is an object of the present invention to distribute over a relatively large area in a uniform manner a hardener coating, on the one hand, as well as to provide a uniform distribution of a polymerizable material, so that with the wrapper of the invention there will be a uniform transfer from the elastic, flexible condition into a mechanically rigid condition.

The elongated wrapper of the present invention, which is initially flexible and which when wrapped around one or more bodies is adapted to be stretched and to assume a substantially rigid condition, includes an outer, elongated, tubular, elastic envelope means having a generally flat cross-sectional configuration for surrounding one or more bodies while being longitudinally stretched and wrapped around the bodies. This envelope means has an inner surface carrying one of the pair of materials which when combined with each other react to assume a hardened condition, this one material being distributed longitudinally along an inner surface of the envelope means while the other of the materials is situated in the interior of the envelope means between the opposed longitudinally extending wall portions thereof. A separating means is situated in the interior of the envelope means between these materials to separate them from each other so as to prevent them from combining with each other. The separating means has the property of responding to the longitudinal stretching of the envelope means, when the latter is wrapped around one or more of the bodies for assuming a non-separating condition placing the above materials in contact with each other so that they will then combine to assume the hardened condition in response to the stretching and wrapping of the envelope means around one or more bodies. The various materials which are used in the wrapper of the invention are selected so as to be adapted to the particular purposes for which the wrapper is intended. Thus, in all cases, all the materials have the property of being capable of withstanding environmental conditions. Moreover, the outer envelope means is impermeable to fluids and is transparent, and in fact the entire wrapper is transparent when it assumes its hardened condition. However, one of the materials which combine to give the wrapper its hardened condition is initially opaque but has the property of becoming transparent when the materials combine, so that by becoming transparent a visual indication is given of the hardening reaction.

BRIEF DESCRIPTION OF DRAWINGS

The invention is illustrated by way of example in the accompanying drawings which form part of this application and in which:

FIG. 2 is a transverse sectional elevation of the wrapper of the invention showing in greater detail how the various layers of FIG. 1 coact with each other;

FIG. 3 is a fragmentary longitudinal sectional elevation of the wrapper of FIG. 2 showing additional details thereof;

FIG. 4 illustrates one example of how the wrapper of the invention may be used;

FIG. 5 is a partly sectional elevation of a fastener means which may be used with the wrapper of the invention; and FIG. 6 is a top plan view of the fastener of FIG. 5.

DESCRIPTION OF PREFERRED EMBODIMENTS

Figure 1:
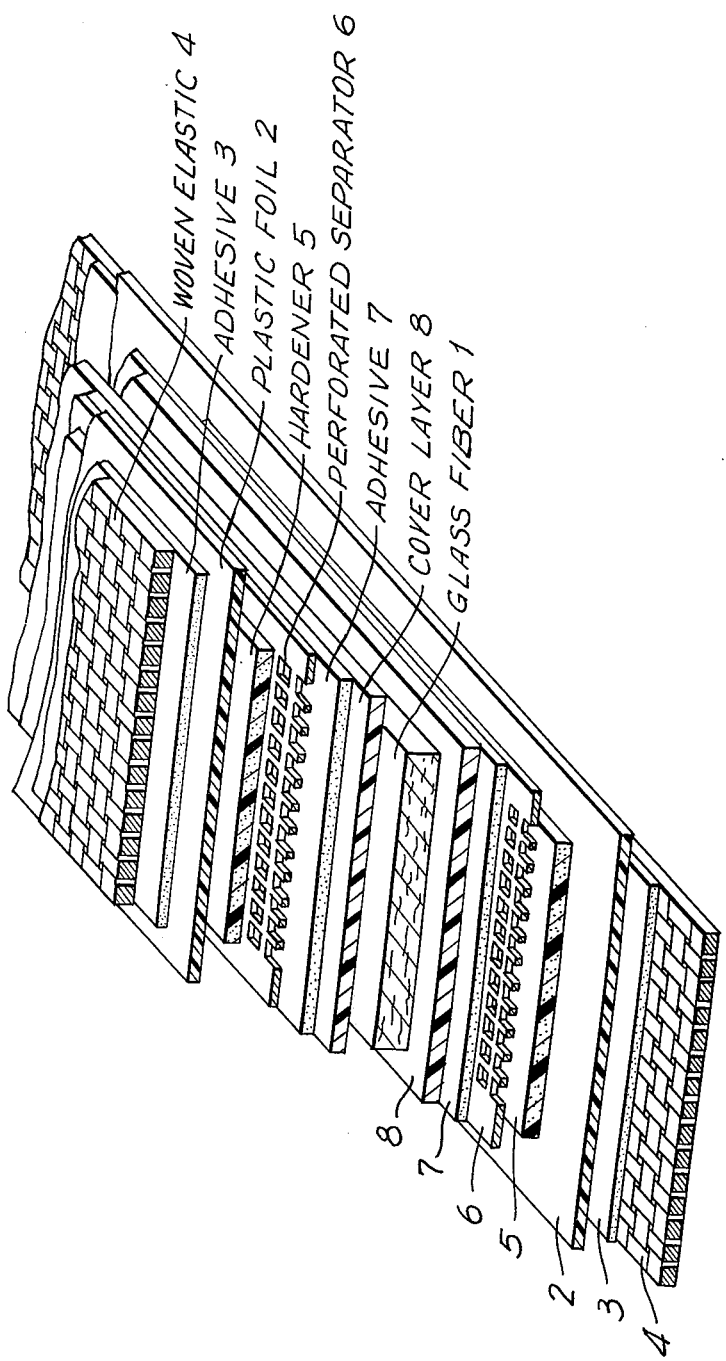
FIG. 1 is a schematic fragmentary perspective illustration of various layers of material which form one embodiment of a wrapper of the invention.

In the description which follows the invention is described in connection with its use in the field of human or veterinary medicine, but it is to be understood that the wrapper of the invention has many additional uses in industry where it can be used in the electrical, shipbuilding, aircraft, autombile, and other industries at any location where parts are to be united or strengthened by a wrapper which is wrapped in such a way that after wrapping it will assume a rigid condition.

Referring first to FIG. 1, there is illustrated therein a storing means 1 which forms the innermost part of the wrapper of the invention. This storing means 1 takes the form of a reinforcing or strengthening material composed of a fleece of glass fibers which is thoroughly impregnated with a polymerizable material such as an unsaturated polyester resin, with the storing means 1 acting in the manner of a sponge for holding the polymerizable material in a relatively stable condition uniformly distributed within the wrapper of the invention. The unsaturated polyester resin which is neither too brittle nor too elastic has mechanical stiffness characteristics which are adapted to the particular use for which the wrapper is designed.

The glass fiber fleece layer 1 which is impregnated with the polymerizable material is situated within an envelope means 10 which is shown in a transverse view in FIG. 2. This envelope means 10 is made up of an inner layer 12 of plastic foil and an outer layer 14 of a woven elastic material which gives to the foil 12 the required elasticity, in a manner described in greater detail below. The plastic foil layer 12 of the envelope means 10 is made up of a pair of ribbons or strips 2 of plastic foil, these bands or ribbons 2 being joined together at their side edges so as to form the enclosure in which the storing means 1 is located together with the polymerizable material. For this purpose the pair of separate strips 2 are welded to each other at their side edges or these side edges may be adhered to each other or seamed together in any manner providing the envelope means 10 with a structure according to which the space within the envelope means is completely enclosed and shut off from the outer atmosphere, this envelope means 10 having the property of being impermeable to fluids. The elongated envelope means 10 is closed at its ends in the same way as at its side edges. The elastic layer 14 of the envelope means 10 is made up of a pair of woven elastic sheet material layers 4 shown in FIG. 1, these layers being adhered to the exterior surfaces of the strips 2 by the adhesive layers 3 indicated in FIG. 1. The adhesive coatings 3 serve to elastically fix the woven elastic layers 4 to the exterior surface of the foil 2.

The elastic strips 2 thus form a pair of elongated opposed wall portions of the envelope means 10 which has the generally flat configuration shown in FIG. 2, and these strips 2 have inner surfaces which carry one of a pair of materials which, when combined, react to assume a hardened condition. Thus, the inner surfaces of the strips 2 are coated with hardener coatings 5 which when contacted by the unsaturated polyester resin stored by the storing means 1 will provide the polymerization and resulting hardening of the structure. Initially, however, the coatings 5 are separated from the polymerizable material with which the glass fiber fleece 1 is impregnated by a separating means 16 which, as shown in FIG. 2, has a pair of separating portions each provided with opposed side edges joined with the inner surface of the envelope means 2 so as to define with the latter a pair of chambers in which the pair of hardener coatings 5 are respectively maintained in a condition separated from the glass fiber fleece 1 and the polymerizable material with which the latter is impregnated. As is shown particularly in FIG. 1, the separating means is composed of a pair of apertured sheet material layers 6 respectively located directly next to the hardener coatings 5 at the surfaces thereof opposed to the inner surfaces of the strips 2, and by way of an adhesive layer 7 each of the apertured strips of sheet material 6 is joined with a covering sheet material 8 which serves to cover and close the apertures of the sheet material 6, this layer of sheet material 8 having the property of rupturing in response to stretching of the envelope means 10.

The glass-fiber fleece layer 1 is made up of monofilaments each having a fiber diameter of substantially less than 18 $\mu$ (nanometer, nm). Preferably the diameter of each monofilament is between 6 and 12 $\mu$. The individual filaments are coated with an adhesive medium preferably containing silan, such as, for example, a silanol. The monofilaments are elastically connected to each other with a suitable binder.

The above-described layer of glass-fiber fleece is impregnated with the polymerizable material which preferably is an unsaturated polyester resin which is neither too brittle nor too elastic and which corresponds in its mechanical stiffness values to the desired purpose. This glass-fiber fleece is impregnated with such an amount of the polymerizable material that the fleece acts in the manner of a sponge for holding the polymerizable material with the ratio of the polymerizable material per unit of area of the fleece being maintained constant with respect to the amount of hardener coating per unit of area at the inner surface of the envelope means.

A particularly suitable polymerizable material is a physiologically compatible polyester, obtained in a known way, and in which different diols, which have up to 6 carbon atoms, are esterized with a mixture of maleic acid anhydride and phthalic acid anhydride. The refractive indices of the glass fiber fleece and the unsaturated polyester are for the most part identical so that the desired transparency is assured, with the matching of these refractive indices being improved by the addition to the polymerizable material of up to 20% of acrylic and methacrylic acid esters as well as epoxy resins, to improve the transparency. In order to prevent yellowing of the polymerization product an additive capable of absorbing ultraviolet rays is desirable. Also it is desirable to provide the polymerizable material, particularly the unsaturated polyester, with a self-extinguishing or flame-limiting medium such as antimony trioxide, chlorinated paraffin, or the like, so that in this way the polyester will not be easily ignitable. In addition to the above additives the polymerizable material such as unsaturated polyester resin can also contain polymerization inhibitors, aromatic and coloring substances, as well as fillers of different raw materials and corresponding accelerators, preferably on the basis of a tertiary amine.

The plastic foil 2 which forms the inner layer of the envelope means is transparent and is also chemically inert as well as impervious to all fluids, and in addition it is physiologically inert and biologically stable. This plastic foil 2 has a thickness on the order of 6 – 12 $\mu$, and it has a high bending index, which is to say it is greatly resistant to flexing in opposite directions, and in addition it is highly resistant to tearing and impact forces. These requirements are preferably fulfilled by a polyester foil which has all of the required properties except flexibility which is required for better adapting of the wrapper to the surface on which it is wound. The manufacture of the tubular envelope is brought about by joining together the side edges of the foil strips 2 by welding, gluing, and/or seaming, so that the glass-fiber fleece which is impregnated with the polymerizable material is tightly closed on all sides off from the surrounding atmosphere. In order to improve the welding of the poorly weldable polyester foil, it is desirable to coat the foil on the one hand with a polyethylene foil and to provide, on the other hand, an adhering of the strips to each other with an adhesive which is resistant to the polymerizing, preferably a polyurethane adhesive.

The adhesive layer 3 is made up of a transparent corresponding high-molecular, physiologically compatible and biologically stable adhesive having the required adhesive properties with respect to the plastic foil and the woven elastic layer 4. Such an adhesive coating can advantageously be polyvinylisobutylether in dissolved or dispersed form.

The woven elastic layer 4 must have the capability of returning to its original substantially unstretched condition while being highly stretchable longitudinally and of low stretchability transversely, while at the same time also being transparent. These requirements are fulfilled by a weave in which the warp yarns are made of highly elastic fibers such as, for example, polyurethane fibers as well as monofilaments and multifilaments of crinkled synthetic fibers such as polyamide and polyester fibers. The weft yarn is composed of thin monofilaments, preferably dull polyester or polyamide fibers for example in the form of a taffeta weave.

This woven elastic layer with the above-described warp and weft yarns can be manufactured in different ways in accordance with the type of weave and the density thereof. The construction of the weave, however, is specially designed so that shifting of the individual windings of the wrapping with respect to each other is avoided. This is brought about by providing the yarns with a crinkled configuration having individual loops which interlock with each other so that the windings of the wrapping of the invention will be prevented from shifting even when placed around a joint such as an elbow or a knee where there is a relatively high degree of movability. Thus, shifting of the wrapping with respect to the skin is avoided. The weft yarns which are situated between the elastomeric warp yarns in crinkled form, such as monofilament or multifilament polyamide or polyester yarns interlocked with each other because of their looped configuration. Thus, the wrapping of the invention is correspondingly thin, impervious to moisture and capable of being sterilized while at the same time being absolutely inert with respect to human skin and being incapable of biological decomposition. Moreover, the wrappings of the invention can be used by themselves as fixing elements which will not shift with respect to each other.

In order to render the wrapper of the invention physiologically compatible in the field of medicine, it is required that the above-described polyurethane, polyamide, and/or polyester fibers have no coatings in the form of dyes or finishing materials which will result in allergic or other skin-damaging reactions. The physiological inertness of polyester foil and the polyester fibers is clear from the fact that this material cannot have any components extracted therefrom when heated through a range of up to 260° C. As already pointed out above, the raw material for the foils and fibers are absolutely biologically stable and cannot be biologically decomposed. The above-mentioned absolute requirements for physiological inertness and biological stability are fulfilled by the polyester foils and fibers as a completely polymerized product.

In accordance with one of the important features of the present invention, the woven elastic layer 4 is initially placed in stretched condition on the plastic foil 2 which, as described above, is first coated at its exterior with a flexible, transparent and physiologically inert adhesive layer. This fixing of the elastic layer 4 to the foil 2 with the elastic in its stretched condition is required so that the non-flexible and non-stretchable foil used for the strips 2 will be longitudinally compressed and will assume the crinkled condition illustrated in FIG. 3 when the tension is released from the elastic layer 4 so that the latter contracts to assume its substantially relaxed, unstretched condition while the foil itself assumes the condition of crepe. Thus, with the elastic woven layer 4, initially adhered to the plastic foil in stretched condition, the subsequent release of the tension in the elastic will permit the latter to contract while crinkling the foil. In this way the foil 2 which otherwise would have no elastic properties is rendered flexible and stretchable and is capable of conforming to any configuration on a body on which the wrapper is wound. Thus, by way of this expedient the elastic layer of the envelope means provides the latter with the required elasticity.

As was pointed out above, the strips 2 are coated at their inner surfaces with the hardener layer 5. The hardener layer is composed preferably of peroxides preferably benzoil peroxide which is easily dissolved in an organic solvent and by way of a peroxide binder which is not oxidizable, such as preferably polyvinyl acetate, is adhered and fixed to the inner surface of the foil 2 in an amount which has the proper relationship per unit of area to the polymerizable material. For this purpose the outer edge regions of the separating layer 6 are welded to the inner surface of the foil and then the pair of foil strips 2 are welded to each other at their side edges to form the tubular envelope, with the free side edges of the separating layer 6 being situated beyond the peroxide layer 5 against the plastic foil 2.

The non-oxidizable adhesive layer, preferably polyvinyl acetate, as referred to above in addition to adhering the hardener layer 5 to the foil 2 serves also to desensitize the peroxide and increase its stability and in addition serves at the same time as an agent for promoting the combining of the peroxide with the polymerizable material while avoiding an undesirably high exothermic reaction.

In order to achieve as uniform as possible a distribution of the peroxide, the peroxide is uniformly applied with respect to the entire surface of the foil 2 which is coated with the peroxide, with the amount of peroxide corresponding to a desired amount per unit of the polyester, and at the same time the wide extent of distribution over a large area assures a wide-area uniform contact and uniform mixing with the polyester and thus a uniformly controlled polymerization and hardening of the polymerizable material without developing too much heat as a result of the exothermic reaction.

As a result of the fact that the organic peroxide crystallizes out on the inner surface of the adhesive which joins it to the foil, the transparent foil 2 becomes non-transparent. However, during use, which is to say after rupture of the separating means and release of the polymerizable material to flow through the previously closed openings of the apertured layer 6, the combining of the hardener 5 with the polymerizable material results in mixing of the hardener with the polymerizable material and the regaining of the transparent property. As a result of the fact that the structure becomes transparent when used, which is to say the separating means ruptures in response to stretching of the envelope means to permit the peroxide and polymerizable material to combine, the wrapper of the invention becomes transparent after being wound onto a body and this transfer to the transparent from the non-transparent state gives an indication and measure of the completeness of the combining, which is to say the dissolving or mixing of the hardener with the polymerizable material, so that this reaction can be visually controlled when the wrapper is applied to one or more bodies by being stretched and wound thereon, and it is even possible to control the action in accordance with the visual perception of the transfer from non-transparent to transparent condition. Thus, by noting that the wrapper has assumed a transparent condition it becomes possible for the user to assure himself that the required complete hardening of the polymerizable material has reliably occurred.

Furthermore, the relatively flat configuration of the wrapper which has a small thickness and a large surface area assures an intense heat transfer to carry away the heat of the exothermic reaction. In order to assure a thorough hardening, a corresponding combination of different organic peroxides with corresponding accelerators and inhibitors is desirable. In particular, the gelling time without reducing the entire hardening time is lengthened in such a way that the readily removable, low-molecular polyester molecules and styrene molecules of the hardener layer are sufficiently active. The amount of additive must have a corresponding relationship with respect to the amount of polymerizable material which is to be hardened, and this may vary in case to case so as to achieve the requirements of a particular application. The above requirements can be reinforced if the polyester has a corresponding make-up and utilizes a combination of different monomers, the selection of which is not critical.

The hardener layers 5 are separated from the polyester-impregnated glass-fiber fleece layer 1 by the separating means which includes the apertured separating sheet material 6 adhered by the adhesive layer 7 to the covering sheet material 8, as pointed out above. The types of apertures with which the sheet material 6 is provided are not critical. It is only necessary to perforate the sheet material 6 in such a way that after mechanical rupture of the covering sheet material 8 there will be sufficient contact between the hardener and the polymerizable material. In order to avoid an undesirable premature contact between the polyester-impregnated glass-fiber fleece and the hardener layer 5, the perforated or apertured sheet material 6 is welded at its side edges, laterally beyond the peroxide layer 5, with the foil 2, or the side edge regions of the sheet material 6 can be glued to the inner surface of the foil 2 by utilizing an adhesive which is inert with respect to polyester. The apertured sheet material 6 which preferably is made of a saturated polyester is transparent and resistant to water and chemicals, has an extremely small thickness, and is inert with respect to the polymerizable material and the hardener. The perforated sheet material 6 is coated with the adhesive layer 7 which preferably is polyurethane, which is also inert with respect to the polymerizable material and the hardener, so that the covering sheet material 8 of the separating means may be fixed with the apertured sheet material 6 while remaining inert with respect to the polymerizable material. The transparent covering sheet material 8 which is inert with respect to the polymerizable material and the hardener and which has a suitable mechanical stiffness must be so brittle that as a result of the flexible deformability of the foil 2, or in other words of the outer envelope means, to the inner surface of which it is fixed together with the apertured sheet material 6, the sheet material 8 will become mechanically ruptured as a result of the flexible deforming of the wrapper of the invention and thus will release or uncover the openings of the sheet material 6. For use as the covering sheet material 8 urea formaldehyde resin has proved to be particularly suitable, this latter material being inert with respect to the hardener and polymerizable material. The separating or covering sheet material 8 ruptures in response to the flexible deformation of the foil 2 as well as from simple hand-pressure and also as a result of the longitudinal stretching of the envelope means when the latter is wrapped around one or more bodies. The mechanical rupturing of the covering sheet material provides particles of the sheet material 8 which become embedded in the product of polymerization after polymerizing of the polymerizable material with which the glass-fiber fleece 1 is impregnated, without causing in this way any loss in the mechanical stiffness or transparency of the polymerized product.

In a special embodiment of the invention the wrapper is provided at its exterior surface with a plastic layer 20, shown at the lower part of FIGS. 2 and 3, composed in a known way of plastic sheets which enclose air bubbles so as to form a cushion layer for protecting the skin of an individual on to which the wrapper is wound. Thus, when in the field of medicine prominent parts of the body are to be protected against rubbing and chafing, the wrapper of the invention will maintain the desirable transparency while at the same time protecting the skin of the individual against injury as a result of the presence of the cushion layer 20. While this layer may be first placed over the skin before the wrapper of the invention is applied it is also possible to adhere the layer of air cushions 20 to the wrapper to form a part thereof with the layer 20 being placed in contact with the skin.

The manufacturing of the wrapper structure of the invention takes place with known methods for manufacturing tapes which are applied with coatings, while at the same time, of course, providing the requirements for the wrapper of the invention.

The immobilizing wrapper of the invention provides in itself, even at thicknesses of only 1 mm such a high degree of mechanical stability that circular wrapping of one convolution substantially entirely upon another is not required for a body part in the field of medicine. Instead the wrapper of the invention can be wound spirally with a relatively small amount of overlap from one convolution to the next on parts of the body such as joints at the elbow and knee, and the wrapper of the invention will prevent build-up of moisture as was undesirably encountered with previously known plaster or plastic bandages which because of their relatively small degree of mechanical stiffness had to be circularly wound a number of times, and thus the wrapper of the invention will avoid any maceration or damaging of the covered skin.

The manner in which the wrapper of the invention is spirally wound on a joint such as an elbow is illustrated schematically in FIG. 4. Thus FIG. 4 shows a wrapper 22 of the present invention spirally wound on an elbow of an individual. As a result of this spiral winding there will be several convolutions which overlap each other. In order to assure against shifting of the winding in a longitudinal direction, which is important in the case of vertically arranged windings in the field of medicine, so as to provide a sufficient stability and immobilization for the body part, the overlapping or crossing windings as well as the ends of the wrapper should be fixed to each other. This fixing can be provided with suitable fastener means 24, a pair of which are schematically represented in FIG. 4, with the details of the fastener means 24 being shown in FIGS. 5 and 6. It will be seen that this fastener means 24 has a pushbutton type of construction. The entire fastener means 24 is preferably made of transparent polystyrene and at one end has a head 26 provided with a relatively stable pointed shank 28 which pierces through the wrapper 22 and snaps into a receiver portion 30 of the fastener means 24. Thus, the parts 26, 30 are interconnected by a springy U-shaped portion 32 which is integral with the parts 26 and 30 enabling the part 30 to be placed between the skin and the wrapping while the part 26 is located at the exterior of the wrapping to be pushed into the receiver 30, snapping into the latter while piercing through the wrapping and thus fastening a pair of overlapping wrapper portions to each other. Additional fixing of the fastened wrapper portions to each other is achieved with this construction in that the monomer portion of the polymerizable material such as styrene is released from the shank 28 which is made of polystyrene and thus in a manner similar to a rivet the shank undergoes a fixed connection with the polymerizable material in the interior of the wrapper of the invention. The receiver portion 30 and the pushbutton portion 26 close tightly together and prevent any running out or leakage of the highly viscous polymerizable material during the polymerizing phase, so that there is no undesirable leakage of the polymerizable material from the wrapper of the invention. Because of the presence of the U-shaped portion 32 it is possible to slip the part 30 between the skin and the wrapping to the desired location, and the operator can place a finger between the part 30 and the skin as well as a thumb over the part 26 pressing the parts 26 and 30 together without causing any undesirable pressure on the body part.

The finished wrapper structure of the invention is protected by being placed in a closed container which is impervious to water and ultraviolet rays. The cushioning layer 20 also serves to prevent undesirable vibration of the wrapper while it is stored and thus a premature rupturing of the separating means with premature hardening in the container is avoided. In accordance with the particular environmental conditions, certain adaptations are made. Thus, in relatively hot climates and in relatively cold zones, in order to assure a sufficient polymerizing of the polymerizable material it is necessary to vary the amount of hardener with respect to the amount of polymerizable material. Thus, in relatively cold climates the amount of hardener supplied per unit of polymerizable material is greater while in relatively hot climates the amount of hardener provided per unit of polymerizable material is less.

What is claimed is:

1. In an elongated wrapper which is initially flexible and which when wrapped around one or more bodies is adapted to be stretched and to assume a substantially rigid condition, outer, elongated, tubular, impermeable, elastic envelope means having in a transverse direction a width which is a relatively small fraction of its length in a longitudinal direction and having a generally flat cross sectional configuration for surrounding one or more bodies while being stretched in said longitudinal direction and wrapped around the bodies, said envelope means having an inner surface carrying one of a pair of materials which when they combine react to assume a hardened condition, said one material being distributed in said longitudinal direction along said inner surface of said envelope means and the other of said materials being situated in the interior of said envelope means between opposed wall portions thereof which extend in said longitudinal direction, and separating means situated in the interior of said envelope means between said materials and separating the latter from each other for preventing them from combining with each other, said separating means including an apertured layer of sheet material and a covering sheet material which is relatively brittle and which has the property of rupturing in response to stretching of said envelope means in said longitudinal direction when said envelope means is wrapped around one or more of said bodies, said covering sheet material being adhered to and covering said apertured sheet material to close the apertures thereof so that upon rupturing of said covering sheet material in response to said longitudinal stretching of said envelope means, said separating means will assume a non-separating condition placing said materials in contact with each other through apertures of said apertured sheet material so that they will combine to assume said hardened condition in response to stretching of said envelope means in said longitudinal direction and wrapping of said envelope means around one or more bodies, said envelope means and separating means both being transparent while said pair of materials include a material which initially is non-transparent but which becomes transparent when said pair of materials combine with each other, so that the transparency resulting from the combining of said pair of materials gives a visual indication of the hardening reaction and renders visible that part of a body which is covered by the wrapper.

2. The combination of claim 1 and wherein a storing means extends longitudinally along the interior of said envelope means for storing said other material therein.

3. The combination of claim 2 and wherein said storing means is in the form of a layer of glass fibers impregnated with the other of said materials.

4. The combination of claim 1 and wherein said opposed wall portions of said envelope means each extend transversely between opposed side edge regions of said envelope means, and said one material being distributed longitudinally along and coating inner surfaces of said opposed wall portions to provide a pair of longitudinally extending coatings of said one material respectively carried by said inner surfaces of said opposed wall portions of said envelope means, said separating means having a pair of separating portions respectively connected with said oppposed wall portions of said envelope means and defining with the latter a pair of elongated chambers in which said coatings are located while being prevented from combining with the other of said materials, said other material being situated in said envelope means between said portions of said separating means.

5. In an elongated wrapper which is initially flexible and which when wrapped around one or more bodies is adapted to be stretched and to assume a substantially rigid condition, outer, elongated, tubular, impermeable, elastic envelope means having in a transverse direction a width which is a relatively small fraction of its length in a longitudinal direction and having a generally flat cross sectional configuration for surrounding one or more bodies while being stretched in said longitudinal direction and wrapped around the bodies, said envelope means having an inner surface carrying one of a pair of materials which when they combine react to assume a hardened condition, said one material being distributed in said longitudinal direction along said inner surface of said envelope means and the other of said materials being situated in the interior of said envelope means between opposed wall portions thereof which extend in said longitudinal direction, and separating means situated in the interior of said envelope means between said materials and separating the latter from each other for preventing them from combining with each other, said separating means including an apertured layer of sheet material and a covering sheet material adhered to and covering said apertured sheet material to close the apertures thereof, said covering sheet material being relatively brittle and having the property of rupturing when responding to stretching of said envelope means in said longitudinal direction when said envelope means is wrapped around one or more of said bodies for providing for contact of said pair of materials through apertures of said apertured sheet material to place said separating means in a condition assuming a non-separating condition placing said materials in contact with each other so that they will combine to assume said hardened condition in response to stretching of said envelope means in said longitudinal direction and wrapping of said envelope means around one or more bodies, said envelope means including an inner tubular layer of plastic foil and an outer layer of elastic material joined to said foil, said foil being in a crinkled condition compressed in said longitudinal direction while said elastic material yieldably resists elongation of said foil in said longitudinal direction to lend elasticity to said foil.

6. The combination of claim 5 and wherein said layer of elastic material is in the form of a woven layer made up of elastic weft and warp yarns with said warp yarns having a greater elasticity than said weft yarns to provide said envelope means with a degree of longitudinal elasticity which is substantially greater than the degree of transverse elasticity.

7. The combination of claim 6 and wherein said yarns of said woven layer of elastic material include yarns having loops therein to provide for interlocking of the windings of the outer envelope means when the latter is wrapped around one or more bodies to prevent slipping of the windings.

8. The combination of claim 1 and wherein said envelope means carries at its exterior a cushioning layer composed of a layer of plastic material enclosing air bubbles therein.

9. The combination of claim 1 and wherein said outer envelope means includes an inner layer of plastic foil which is impermeable to all fluids and which is transparent, said plastic inner layer of said envelope means carrying at its exterior a woven elastic layer of substantial longitudinal stretchability and relatively small transverse stretchability with said elastic layer being adhered to said plastic foil by a transparent, high-molecular, elastic adhesive layer of polyisobutylether and said plastic foil being in a longitudinally crinkled condition while said elastic layer is substantially relaxed so that the latter yieldably resists elongation of said plastic foil to lend elasticity thereto.

10. The combination of claim 7 and wherein said plastic foil of said outer envelope means has said opposed longitudinally extending wall portions each of which extends transversely between opposed side edges of said envelope means and said longitudinally extending wall portions respectively having inner surfaces coated with said one of said pair of materials, the other of said pair of materials being a polymerizable material while said one material is a hardener, for the polymerizable material, and said separating means having a pair of elongated separating portions each of which has opposed side edges joined to the inner surface of said envelope means and said pair of separating portions defining with said plastic foil of said envelope means a pair of longitudinally extending chambers in which said hardener coatings are maintained separated from said polymerizable material.

11. The combination of claim 10 and wherein said hardener coatings are adhered to said inner surfaces of said opposed wall portions of said foil by a transparent, non-oxidizing material which is easily dissolved in an organic solvent medium and which is inert with respect to the polymerizable material.

12. The combination of claim 10 and wherein said separating means includes an apertured sheet material situated next to each coating and made of a transparent foil which is inert with respect to the hardener coating and polymerizable material, said covering sheet material being made of a urea formaldehyde resin which is transparent, relatively brittle and subject to rupturing, and inert with respect to the polymerizable material and the hardener coating.

13. The combination of claim 12 and wherein said covering sheet material and said apertured sheet material are adhered to each other by a layer of polyurethane.

14. The combination of claim 10 and wherein a storing means stores said polymerizable material and is in the form of a layer of glass fibers impregnated with said polymerizable material and having a refractive index substantially the same as the refractive index of said polymerizable material to be relatively transparent while said envelope means and separating means are also transparent.

15. The combination of claim 10 and wherein said polymerizable material is an unsaturated polyester resin.

16. The combination of claim 15 and wherein said unsaturated polyester resin has a diol component composed of glycol up to 6 carbon atoms.

17. The combination of claim 15 and wherein said unsaturated polyester resin contains an additive of up to 20% selected from the group consisting of acrylic acid esters, methacrylic acid esters, and epoxy resins.

18. The combination of claim 10 and wherein the polymerizable material contains an additive capable of absorbing ultraviolet rays.

19. The combination of claim 10 and wherein said polymerizable material contains an additive selected from the group consisting of self-extinguishing or flame-limiting materials.

20. The combination of claim 10 and wherein said polymerizable material contains polymerization inhibitors.

21. The combination of claim 10 and wherein said polymerizable material is combined with an accelerator.

22. The combination of claim 10 and wherein said polymerizable material is provided with coloring additives.

23. The combination of claim 10 and wherein said polymerizable material is provided with a filler of raw materials.

24. The combination of claim 10 and wherein said polymerizable material is maintained in the interior of said envelope means by a storing means in the form of a fleece layer of glass fibers which act in the manner of a sponge for storing said polymerizable material in a manner distributing the polymerizable material uniformly with a given amount of polymerizable material being provided for each unit of surface area of said envelope means.

25. The combination of claim 24 and wherein said glass fiber fleece is composed of individual monofilaments which are flexibly and elastically fixed to each other.

26. The combination of claim 24 and wherein the glass fiber fleece is coated with a silane-containing adhesive medium.

27. The combination of claim 8 and wherein said elastic layer is woven from warp yarns selected from the group consisting of highly elastic polyurethane and crinkled, loop-forming, self-interlocking polyamide and polyester fibers, and weft monofilaments selected from the group consisting of crinkled, looped, self-interlocking polyester and polyamide fibers.

28. The combination of claim 1 and wherein said other material is a polymerizable material while said one material is a mixture of organic peroxides.

29. The combination of claim 1 and wherein said other material is a polymerizable material while said one material is a hardener material mixed with a polyvinyl acetate-containing adhesive medium.

30. The combination of claim 1 and wherein said envelope means and separating means are both transparent while said other material is a transparent polymerizable material, said one material being a hardener material uniformly distributed witha given amount of hardener material for each unit of area and composed of an amount of peroxide which is non-transparent until combined with the polymerizable material.

31. The combination of claim 1 and wherein said other material is a polymerizable material while said one material is a hardener layer joined to the inner surface of said envelope means, and said separating means including a separating layer extending around said hardener layer and having opposed edges welded or adhered to the inner surface of said envelope means to define with the latter a chamber in which said hardener layer is maintained separate from said other material.

32. The combination of claim 1 and wherein said pair of materials are respectively, a polymerizable material and a hardener therefor, releasable fastener means coacting with windings of the wrapped envelope means and the structure therein for fastening them to each other, said releasable fastener means including a push member having a pointed shank to pierce through the wrapping and a receiving member having a recess for receiving the pointed shank, and said shank being made of polystyrene while said polymerizable material is a polyester with which said polystyrene becomes bonded so that the polymerizable material will be united with said shank.

* * * * *